US00PP36074P3

(12) United States Plant Patent
Rietberg

(10) Patent No.: US PP36,074 P3
(45) Date of Patent: Aug. 20, 2024

(54) ***HEBE* PLANT NAMED 'Arona'**

(50) Latin Name: ***Hebe* hybrid**
Varietal Denomination: Arona

(71) Applicant: Henrik Christiaan Cozijn Rietberg, Wezep (NL)

(72) Inventor: Henrik Christiaan Cozijn Rietberg, Wezep (NL)

(73) Assignee: EDENS CREATIONS BV, Wezep (NL)

( * ) Notice: Subject to any disclaimer, the term of this patent is extended or adjusted under 35 U.S.C. 154(b) by 0 days.

(21) Appl. No.: 18/383,528

(22) Filed: Oct. 25, 2023

(65) Prior Publication Data

US 2024/0155959 P1 May 9, 2024

(30) Foreign Application Priority Data

Nov. 3, 2022 (QZ) ..... PBR 2022/2455

(51) Int. Cl.
*A01H 5/02* (2018.01)
*A01H 6/00* (2018.01)
*A01H 6/68* (2018.01)

(52) U.S. Cl.
USPC ..... Plt./251
CPC ..... *A01H 6/00* (2018.05)

(58) Field of Classification Search
USPC ..... Plt./251
See application file for complete search history.

*Primary Examiner* — Susan McCormick Ewoldt
*Assistant Examiner* — Zachariah Allan Kay
(74) *Attorney, Agent, or Firm* — Penny J. Aguirre

(57) ABSTRACT

A new cultivar of *Hebe* plant named 'Arona' that is characterized by its consistently healthy plants with a low susceptibility to leaf spot disease and downy mildew, its compact plant habit, its small leaves, its flowers that are intense red-purple in color, and its self-cleaning flowers.

1 Drawing Sheet

Botanical classification: *Hebe* hybrid.
Cultivar designation: 'Arona'.

CROSS REFERENCE TO A RELATED APPLICATION

This application claims priority to European Community Plant Variety Office (CPVO) Plant Breeder's Rights Application No. 2022/2455 filed on Nov. 3, 2022, under 35 U.S.C. 119(f), the entire contents of which is incorporated by reference herein.

BACKGROUND OF THE INVENTION

The present invention relates to a new and distinct cultivar of *Hebe*, botanically of hybrid origin, known as *Hebe* 'Arona', and will be referred to hereafter by its cultivar name, 'Arona'. 'Arona' is an evergreen shrub grown for use as a container plant and as a landscape shrub.

The new cultivar was derived from a controlled breeding program conducted by the Inventor in Wezep, The Netherlands. The objectives of the breeding program are to select new cultivars of *Hebe* with improved plant health, compact plant habits, small leaves, abundant flowering, vibrant and solid flower colors, and self-cleaning flowers. The new cultivar arose from a cross made in August of 2017 between unnamed and unpatented proprietary plants from the Inventor's breeding program; reference no. HM17-208 as the female parent and ref no. PM17-308 as the male parent. The Inventor selected 'Arona' in August of 2018 as a single unique plant amongst the seedlings that resulted from the above cross.

Asexual propagation of the new cultivar was first accomplished by stem cuttings in September of 2017 by the Inventor in Wezep, The Netherlands. Asexual propagation by stem cuttings has determined the characteristics of the new cultivar are stable and reproduced true to type in successive generations.

SUMMARY OF THE INVENTION

The following traits have been repeatedly observed and represent the characteristics of the new cultivar, which in combination distinguish 'Arona' as a new and distinct cultivar of *Hebe*.

1. 'Arona' exhibits consistently healthy plants with a low susceptibility to leaf spot disease and downy mildew.
2. 'Arona' exhibits a compact plant habit.
3. 'Arona' exhibits small leaves.
4. 'Arona' exhibits flowers that are intense red-purple in color.
5. 'Arona' exhibits self-cleaning flowers.

The female parent of 'Arona' differs from 'Arona' in having leaves that are lighter green in color, flowers that are less intense red-purple in color, and a shorter blooming period. The male parent of 'Arona' differs from 'Arona' in having a less compact plant habit, leaves that are lighter green in color, flowers that are less intense red-purple in color, and a shorter blooming period. 'Arona' can be most closely compared to the *Hebe* cultivars 'Wiri Charm' (not patented) and 'Zenia' (not patented). Both 'Wiri Charm' and 'Zenia' are both similar to 'Arona' in plant vigor and in having an abundant flowering habit. 'Wiri Charm' differs from 'Arona' in having a less compact plant habit, leaves that are larger in size, a flowering period that commences later in the season, and flowers that are less intense red-purple in color. 'Zenia' differs from 'Arona' in having a less compact plant habit, leaves that rounder in shape with an obtuse apex, a flowering period that commences later in the season, and flowers that are less intense and more purple in color.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosures and/or sales that fall within a one-year grace period to the filing date. Disclosures include website listings by Plantarium, All Blooms, floramedia, h, Horticulture Week, BPnieuws, Goedemorgen Roos, and FloraNews.

BRIEF DESCRIPTION OF THE DRAWING

The accompanying color photograph illustrates the overall appearance and distinct characteristics of the new *Hebe*. The photograph was taken of a 5-month-old plant of 'Arona' as grown outdoors in a 10-cm container in Wezep, The Netherlands. The photograph is a side view of 'Arona' in bloom. The colors in the photograph may differ slightly from the color values cited in the detailed botanical description, which accurately describe the colors of the new *Hebe*.

DETAILED BOTANICAL DESCRIPTION OF THE PLANT

The following is a detailed description of 5-month-old plants of the new cultivar as grown outdoors in 10-cm containers in Wezep, The Netherlands. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming period*.—From summer into fall in The Netherlands.

*Plant type*.—Evergreen shrub.

*Plant habit*.—Compact.

*Height and spread*.—Average of 60 cm in height and spread in the landscape.

*Cold hardiness*.—At least to U.S.D.A. Zone 8.

*Diseases and pest*.—Observed to have low susceptibility to leaf spot disease (*Septoria veronicae*) and downy mildew (*Perenospora* ssp.), no susceptibility or resistance to pests has been observed.

*Root description*.—Fibrous to slightly fleshy.

*Propagation*.—Softwood stem cuttings.

*Root development*.—Root initiation occurs in 3 weeks in summer and 6 weeks in winter, time to produce a rooted cutting is 2 months.

*Growth rate*.—Moderate.

Branch description:

*Branch size*.—Average of 18 cm in length and 2.5 mm in diameter.

*Branch shape*.—Round.

*Branch color*.—Young; 183D, mature; 148A and 144B, internodes 144A, bark; N199A.

*Branch surface*.—Densely covered with very short glandular hairs; 0.1 mm in length, matches surface color.

*Branch strength*.—Strong.

*Internode length*.—Average of 1.5 cm.

*Branching habit*.—3 main branches, 6 lateral branches.

Foliage description:

*Leaf shape*.—Obovate, slightly carinate.

*Leaf division*.—Single.

*Leaf base*.—Cuneate.

*Leaf apex*.—Bluntly acute.

*Leaf venation*.—Pinnate, color upper surface; 146D, color lower surface; 147A.

*Leaf margins*.—Entire.

*Leaf attachment*.—Petiolate.

*Leaf arrangement*.—Opposite.

*Leaf surface*.—Both surfaces smooth, glabrous, non-rugose, upper surface moderately glossy, lower surface matte to very slightly glossy.

*Leaf color*.—Young upper surface; 137A, young lower surface; 146B, mature upper surface; a blend of NN137A and 147A, mature lower surface; a blend of 146A and 146B.

*Leaf number*.—Average of 20 per lateral branch 18 cm in length.

*Leaf size*.—An average of 4.2 cm in length and 1.4 cm in width.

*Petioles*.—3 mm in length, 1 mm in diameter, flattened, both surfaces are smooth, glabrous, and very slightly glossy, strong, both surfaces 144B in color.

Flower description:

*Inflorescence type*.—Raceme.

*Inflorescence size*.—Average of 4.9 cm in height and 2.5 cm in width.

*Inflorescence lastingness*.—About 7 days, self-cleaning.

*Flower shape*.—Campanulate.

*Flower fragrance*.—None.

*Flower quantity*.—Average 80 flowers per inflorescence, 600 flowers per plant, 5,500 flowers and flower buds per plant.

*Flower arrangement*.—Axillary racemes.

*Flower aspect*.—Outward.

*Flower size*.—Average of 8 mm in height and diameter, 9 mm in depth, throat 2 mm in diameter, flower tube 3.5 mm in length and 2 mm in diameter.

*Peduncles*.—Strong, 6.8 cm in length and about 1.75 mm in diameter, 146D and N148A in color, held at about a 32.5° angle to vertical, surface is very slightly glossy and densely covered with very short glandular hairs; an average of 0.1 mm in length, color matches surface color.

*Pedicels*.—Strong, average of 4 mm in length and 0.4 mm in diameter, held at about a 50° angle to peduncle, N148A in color.

*Flower buds*.—Narrow elliptic, 5.5 mm in length and 2 mm in diameter, narrow elliptic to lanceolate in shape, color; 58A, changing to 77B towards the calyx, immature calyx 147A, surface is matte, smooth and glabrous.

*Calyx*.—Rotate-shaped, average of 3 mm in length and 2 mm in diameter.

*Sepals*.—4, narrow ovate in shape with entire margins, upper sepals 2.5 mm in length, lower sepals 3 mm in length, upper and lower sepals are 1 mm in width, rotate, acute tip, base cuneate and fused, both surfaces glabrous, upper surface matte, lower surface slightly glossy, color; when opening and fully open upper surface 137B, when opening and fully open lower surface 137A.

*Petals*.—Average 4, 1 whorl, upper petal very slightly concave, lower and lateral petals moderately reflexed, upper petals; 4 mm in length and 3 mm in width, lateral and lower petals; 3.5 mm in length, 2.5 mm in width, all petals; entire margins, apex obtuse, upper and lower surface is smooth, glabrous, non-rugose, and slightly glossy, color: when opening upper surface; 61C, when opening lower surface; 58A, base 64C, when fully open upper surface; 64C, when fully open lower surface; 64C, upper surface fading to N66C, base N66D, lower surface fading to N66D, throat color; 77A, tube; inner surface 77A in color, outside surface 77B in color.

*Floral bracts*.—A single bract is placed below each individual flower, narrow ovate in shape and concave, tip acute, cuneate base, 1.5 mm in length, 0.5 mm in width, both surfaces glabrous, both surfaces 146B in color.

Reproductive organs:

*Gynoecium*.—Pistil; 1, 7 mm in length, stigma; 0.5 mm in diameter, club-shaped, 77B in color, style; 6.5 mm in length and 69A in color, ovary; 143C in color.

*Androecium*.—Stamens: 2, anthers; dorsifixed, oblong in shape, 1.5 mm in length, 0.5 mm in width and 183B in color, filaments; 5 mm in length, 69A in color, pollen; none observed.

*Fruit and seed*.—None observed to date.

It is claimed:

1. A new and distinct cultivar of *Hebe* plant named 'Arona' as herein illustrated and described.

* * * * *

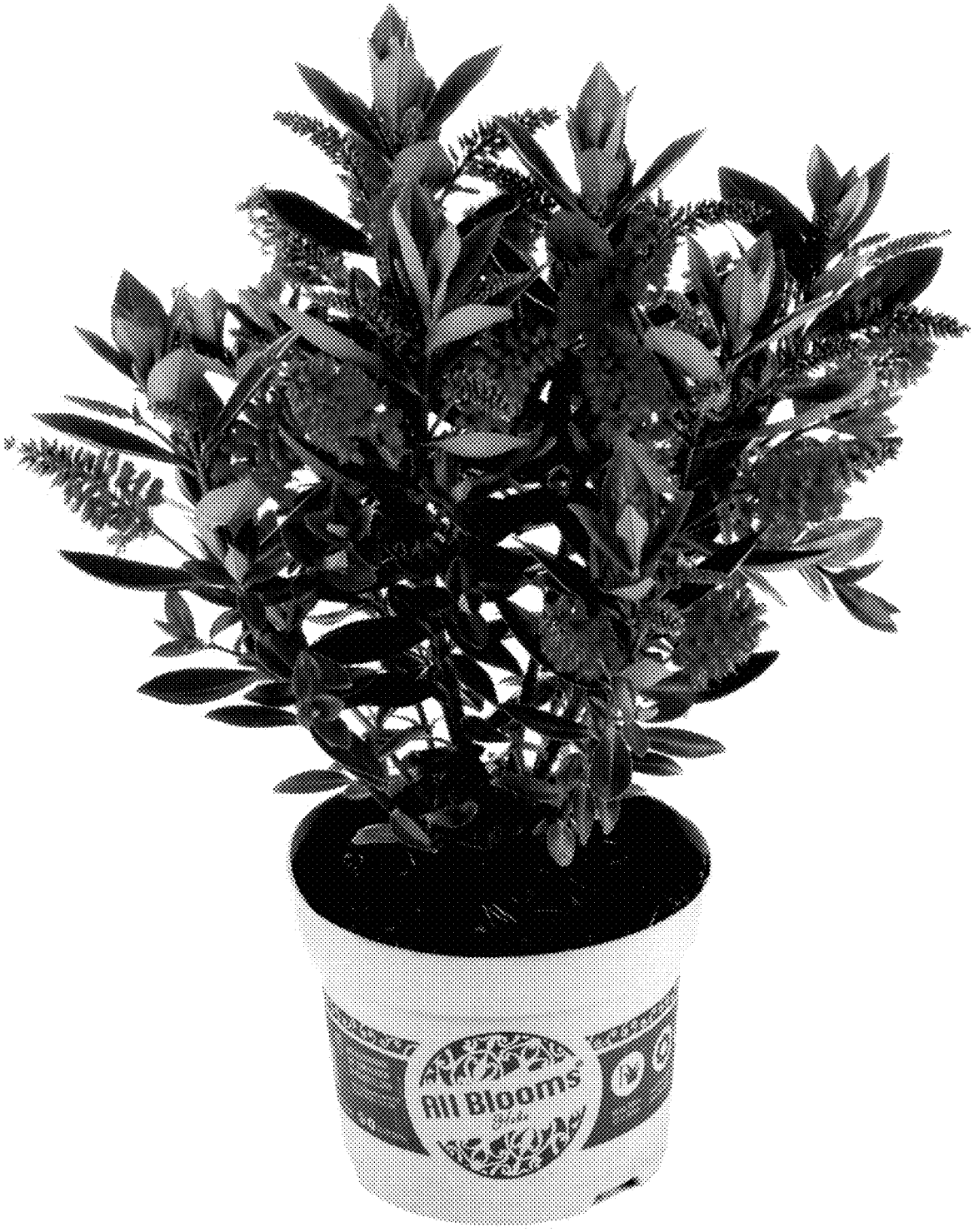
All Blooms